United States Patent
Li et al.

(10) Patent No.: US 7,507,768 B2
(45) Date of Patent: Mar. 24, 2009

(54) ANTIDIABETIC FORMULATION AND METHOD

(75) Inventors: Danping Li, East Brunswick, NJ (US); Lawan Phusanti, Lafayette, NY (US); Divyakant S. Desai, West Windsor, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 192 days.

(21) Appl. No.: 11/668,536

(22) Filed: Jan. 30, 2007

(65) Prior Publication Data

US 2007/0141154 A1    Jun. 21, 2007

Related U.S. Application Data

(62) Division of application No. 10/023,533, filed on Dec. 17, 2001, now Pat. No. 7,183,321.

(51) Int. Cl.
*A61K 31/155* (2006.01)
*A61K 31/425* (2006.01)

(52) U.S. Cl. ..................... 514/635; 514/369

(58) Field of Classification Search ................. 514/635, 514/369
See application file for complete search history.

(56) References Cited

U.S. PATENT DOCUMENTS

| | | | |
|---|---|---|---|
| 4,327,725 A | | 5/1982 | Cortese et al. |
| 4,612,008 A | | 9/1986 | Wong et al. |
| 5,024,843 A | | 6/1991 | Kuczynski et al. |
| 5,082,668 A | | 1/1992 | Wong et al. |
| 5,091,190 A | | 2/1992 | Kuczynski et al. |
| 5,356,896 A | * | 10/1994 | Kabadi et al. ............ 514/256 |
| 5,545,413 A | | 8/1996 | Kuczynski et al. |
| 5,591,454 A | | 1/1997 | Kuczynski et al. |
| 5,922,769 A | * | 7/1999 | Barelli et al. ............ 514/616 |
| 6,011,049 A | | 1/2000 | Whitecomb |
| 6,031,004 A | * | 2/2000 | Timmins et al. ........... 514/635 |
| 6,099,862 A | | 8/2000 | Chen et al. |
| 6,117,451 A | | 9/2000 | Kumar |
| 6,284,275 B1 | | 9/2001 | Chen et al. |
| 6,303,146 B1 | * | 10/2001 | Bonhomme et al. ......... 424/465 |
| 6,524,618 B1 | | 2/2003 | Kumar et al. |
| 6,586,438 B2 | * | 7/2003 | Piper ........................ 514/12 |
| 2002/0177602 A1 | | 11/2002 | Piper |
| 2003/0021841 A1 | * | 1/2003 | Matharu et al. ............ 424/465 |

FOREIGN PATENT DOCUMENTS

| | | |
|---|---|---|
| WO | WO 00/12097 | 3/2000 |
| WO | WO 00/28989 | 5/2000 |

OTHER PUBLICATIONS

Pharmacy, Fourth Edition, p. 346, Dec. 2000.
Vasudevan, M. et al, J. Pharm. Biomed. Anal., 25, 77-84 (2001).
Cefalu, W.T. et al., "Combination Glipizide GITS/Metformin Normalizes Glucose and Improves Insulin Sensitivity in Hyperinsulinemic Moderately Well Controlled", Diabetes, vol. 45, Suppl. 2, No. 742, p. 201A (1996).
Cefalu, W.T. et al., "Insulin Sensitivity is Improved After Glipizide GITS Monotherapy and in Combination with Metformin", Diabetologia, vol. 39, Suppl. 1, No. 875, p. A231 (1996).
Edwards, I.J. et al., "Combination Glipizide GITS/Metformin Treatment Reduces Low Density Lipoprotein Binding to Arterial Proteoglycans in NIDDM", Diabetes, vol. 46, Suppl. 1, No. 176, p. 45A (1997).
Hollenbeck, C.B. et al., "Combination Glipizide/Metformin Treatment in Non-Insulin Dependent Diabetes (NIDDM)", Diabetes, vol. 39, Suppl. 1, No. 432, p. 108A (1990).
Reaven, G.M. et al., "Combined Metformin-Sulfonylurea Treatment of Patients with Noninsulin-Dependent Diabetes in Fair to Poor Glycemic Control", Journal of Clinical Endocrinology and Metabolism, vol. 74, No. 5, pp. 1020-1026 (1992).

* cited by examiner

*Primary Examiner*—Brian-Yong S Kwon
(74) *Attorney, Agent, or Firm*—Burton Rodney

(57) ABSTRACT

An antidiabetic pharmaceutical formulation is provided, especially adapted for treating Type II diabetes, which includes a combination of metformin and glipizide in a manner to control moisture in the formulation so that the glipizide does not hydrolyze, yet the metformin is compressible, if necessary. A method for treating diabetes is also provided employing the above formulation.

13 Claims, No Drawings

ANTIDIABETIC FORMULATION AND METHOD

This application is a Divisional of Ser. No. 10/023,533, filed Dec. 17, 2001 now U.S. Pat. No. 7,183,321, which is incorporated herein by reference in its entirety

FIELD OF THE INVENTION

The present invention relates to a pharmaceutical formulation and method for treating type 2 diabetes. The formulation includes metformin and glipizide (a sulfonyl urea) in a manner to control moisture in the formulation so that the glipizide does not hydrolyze, yet the metformin is compressible, if necessary.

BACKGROUND OF THE INVENTION

The biguanide antihyperglycemic agent metformin disclosed in U.S. Pat. No. 3,174,901 is currently marketed in the U.S. in the form of its hydrochloride salt (Glucophage®), by the Bristol-Myers Squibb Company.

The diagnosis and management of type 2 diabetes mellitus is rapidly undergoing progressive changes. It is now widely accepted that glycemic control makes a difference. The goal of diabetes therapy today is to achieve and maintain as near normal glycemia as possible to prevent the long-term microvascular and macrovascular complications of an elevated blood glucose. The diagnosis of diabetes has undergone significant changes as evidenced by the new ADA diagnostic and classification guidelines. Oral therapeutic options for the treatment of type 2 diabetes mellitus, until recently, have been severely limited. Prior to 1995, sulfonyl ureas had been the mainstay of oral diabetes agents in the United States. Sulfonyl ureas target one mechanism of hyperglycemia by augmenting insulin secretion from the beta cell. Since 1995, three new classes of agents have been added to the anti-diabetes armamentarium for the management of hyperglycemia. Metformin, a biguanide, targets additional mechanisms of hyperglycemia by inhibiting hepatic glucose production and enhancing peripheral glucose uptake and thereby reducing insulin resistance; thiazolidinediones such as troglitazone, rosiglitazone and pioglitazone decrease peripheral insulin resistance; and alpha-glucosidase inhibitors such as acarbose and miglitol help control postprandial glucose excursion by delaying absorption of dietary carbohydrate. These agents are all indicated as monotherapy and some are indicated for use in combination therapy, generally after monotherapy has been found to be inadequate.

In 1995, metformin was added to sulfonyl urea therapy in patients who had not achieved glycemic control with sulfonyl urea monotherapy, and the two agents were found to have a remarkable effect on glycemic control or lowering of hemoglobin-A1c. The different mechanisms of action in targeting hyperglycemia are complimentary and make combination use attractive and a rational course of action. Prescription data reveals approximately 60% of metformin use is in combination with a sulfonyl urea.

Examples of combinations of metformin and the sulfonyl urea glyburide (also referred to as glibenclamide) are disclosed in documents such as the following:

(1) WO 97/17975 published May 22, 1997, (Barelli et al, Istituto Gentili S.P.A.) and US RE37,330E (hereinafter Barelli et al) discloses a combination of glibenclamide and metformin in a 1:100 weight ratio, so as to allow a daily dosage of 15 mg glibenclamide and 1500 mg metformin, used for the onset of diabetes to the most severe cases, particular in cases of secondary failure to a combination of glibenclamide-metformin HCl in a weight ratio higher than 1:100.

(2) Vigneri et al, Treatment of NIDDM Patients with Secondary Failure to Glyburide: Comparison of the Addition of Either Metformin or Bed-Time NPH Insulin to Glyburide, Diabete & Metabolisme, 1991, 17, 232-234, disclose use of a combination of 1.5 g/day metformin and 15 mg/day glyburide to treat NIDDM patients with secondary failure to 15 mg/day glyburide.

(3) Higginbotham et al, Double-Blind Trial of Metformin in the Therapy of Non-Ketotic Diabetes, The Medical Journal of Australia, Aug. 11, 1979, 154-156, discloses treatment of diabetic patients, who were already receiving from 10 mg to 20 mg per day of glibenclamide, with 500 mg metformin twice a day. Higginbotham et al conclude "that in selected diabetics whose condition is inadequately controlled with sulfonylurea therapy, significant improvement in diabetic control can be obtained by the addition of metformin in a low dose of 500 mg twice a day."

(4) U.S. application Ser. No. 09/353,141, filed Jul. 14, 1999 (based on European application No. 98401781.4, filed Jul. 15, 1998) now U.S. Pat. No. 6,303,146 B1 discloses formulations containing metformin and glyburide where the glyburide is of a particular particle size.

Documents which disclose combinations of metformin and glipizide include the following:

(1) Combination of glipizide/metformin treatment reduces low density lipoprotein binding to arterial proteglycans in DIDDM, Edwards et al, Diabetes, (46, Suppl. 1, 45A, 1997).

(2) Combination of glipizide/metformin normalizes glucose and improves insulin sensitivity in hyperinsulinemia moderately well controlled. Cefalu et al, Diabetes, (45, Suppl. 2, 201A, 1996).

(3) Effects of combination of glipizide/metformin treatment on oxidizability of LDL in NIDDM, Crouse et al, Circulation, (94, No. 8, Suppl., I508, 1996).

(4) Insulin sensitivity is improved after glipizide monotherapy and combination with metformin, Cefalu et al, Diabetologia, (39, Suppl. 1, A231, 1996).

(5) Combined Metformin—Sulfonylurea Treatment of Patients with NIDDM in Fair to Poor Glycemic Control, Reaven et al, J. Clin. Endocrinol. Metab. (74, No. 5, 1020-26, 1992).

(6) Combination of Glipizide/Metformin Treatment in NIDDM, Hollenbeck et al, Diabetes, (39, Suppl. 1, 108A, 1990).

(7) Oral Antidiabetic Combination Therapy with Sulfonyl ureas and Metformin, Haupt et al, Med. Welt. (40, No. 5, 118-23, 1989).

(8) Variation of the lipemic pattern in diabetic subjects after treatment with a combination of glipizide and metformin, Ferlito et al, PROGR. MED. (Roma) 31/6 (289-301) 1975.

(9) Results with a combination of glipizide and dimethylbiguanide in 40 cases of diabetes, Parodi et al, GAZZ. MED. ITAL. 132/5 (226-235) 1973.

(10) U.S. Pat. No. 6,099,862, Chen et al, "Oral Dosage Form for the Controlled Release of a Biguanide and Sulfonylurea".

Other combinations of metformin and another antidiabetic agent are disclosed in documents that include the following:

(1) U.S. Pat. No. 5,631,224 to Efendic et al discloses a combination of metformin with GLP-1(7-36) amide or GLP-1(7-37) or a fragment thereof.

(2) WO 98/57634 (SKB) discloses a method for treating diabetes employing a combination of a thiazolidenedione and metformin. The thiazolidenedione may be troglitazone, ciglitazone, pioglitazone or englitazone, and may be employed in dosages of 2 to 12 mg per day while the metformin may be employed in daily dosages "of up to 3000 mg per day, in unit doses of 500 mg (for example, 2 to 3 times per day) or 850 mg (2 times per day), one example of a dosage for metformin is 500 mg building to 5 times per day."

(3) EP 0749751A2 (Takeda) discloses a combination of a thiazolidenedione insulin sensitivity enhancer (such as pioglitazone) and metformin.

Several fixed combinations of metformin and glyburide (glibenclamide) are presently being marketed. These include (1) combinations of 400 mg metformin/2.5 mg glibenclamide (Boehringer's Bi-Euglucon in Argentina, and Bi-Euglicon M in Italy; Guidotti/Menarini's Glibomet in the Dominican Republic and Italy; HMR's Normell in Greece and Hoechst's Suguan-M in Italy; Sun Pharma's Glucored in India; Monsanto's (Searle's) Benclamet in India; Guidotti's Glibomet in Liban; Berlin Chemie/Menarini's Glibomet in the Slovak Rep., and Roche's Bi-Euglucon in Uruguay); (2) combinations of 500 mg metformin/5 mg glibenclamide (Sun Pharma's Glucored in India; Monsanto's (Searle's) Benclamet in India, USV's Duotrol in India; and Lakeside's (Roche) Bi-Euglucon M5 in Mexico); (3) combinations of 500 mg metformin/2.5 mg glibenclamide (Molteni's Glucomide in Italy, Lakeside's (Roche) Bi-Euglucon M in Mexico and Szabo's Dublex in Uruguay); (4) 1 g metformin/5 mg glibenclamide (Silanes Sil-Norboral in Mexico); and (5) Bristol-Myers Squibb's Glucovance®.

The labeling for Glucophage® (Bristol-Myers Squibb's metformin), in the Physicians' Desk Reference 1999, under "Indications and Use", indicates that Glucophage may be used concomitantly with a sulfonylurea. It is further indicated under "Dosage and Administration" "Concomitant Glucophage and Oral Sulfonylurea Therapy" that "If patients have not responded to four weeks of the maximum dose of Glucophage monotherapy, consideration should be given to gradual addition of an oral sulfonylurea while continuing Glucophage at the maximum dose . . . . With concomitant Glucophage and sulfonylurea therapy, the desired control of blood glucose may be obtained by adjusting the dose of each drug. However, attempts should be made to identify the maximum effective dose of each drug to achieve this goal." The recommended dosing schedule for Glucophage® is a starting dose of 500 mg twice a day or 850 mg once a day with dosage increases in increments of 500 mg weekly or 850 mg every 2 weeks up to a total of 2000 mg per day.

Package inserts for Bi-Euglucon M and Suguan M in Italy (400 mg metformin/2.5 mg glibenclamide) indicate that these drug combinations are used in cases of primary or secondary resistance to sulfonyl ureas (that is as second or third line therapy) and that a dosage of ½ tablet per day increasing ½ tablet at a time according to glycemic variations up to 4 tablets per day are employed.

Package inserts for Glibomet (400 mg metformin/2.5 mg glibenclamide) and Glucomide (500 mg metformin/2.5 mg glibenclamide) in Italy indicate that these drug combinations are used for treating type 2 diabetes which is non-controllable or cannot be controlled with only diet or with diet and sulfonyl urea (that is as first line therapy or second line therapy).

The package insert for Glibomet in Italy indicates a daily dosage of 2 tablets, that is 800 mg metformin and 5 mg glibenclamide, up to 2 grams metformin. The package insert for Glucomide in Italy indicates a daily dosage of 2 capsules, that is 1000 mg metformin up to 2 grams metformin, and 5 mg glibenclamide.

Thus, the concomitant use of metformin and a sulfonyl urea, including glipizide, is known. However, the use of metformin and glipizide in a single formulation in accordance with the present invention is not believed to be known in the art. Such a formulation would be highly desirable for patient convenience and to ensure patient compliance, but preparation of such a formulation also requires special care.

Commercially, metformin hydrochloride and glipizide are separately available as tablets. To prepare a metformin/glipizide combination in a single tablet poses many challenges. First, the dose for each agent is very different. Metformin is available commercially as 500 mg, 850 mg and 1000 mg tablets. Glipizide is available as 5 mg and 10 mg tablets. Moreover, glipizide is available as a micronized drug substance. Given the disparity in the doses of the agents and the differences in their particle sizes, content uniformity of glipizide poses significant problems, especially when formulating glipizide with another agent like metformin. Additionally, glipizide is susceptible to hydrolysis. Therefore, the amount of moisture must be controlled. However, at the same time, some residual moisture is necessary to formulate tablets with sufficient hardness from metformin which is poorly compressible. Further, the selection of excipients must be made such that they are compatible with both metformin and glipizide.

In view of the above, it is clear that it would be desirable to provide metformin and glipizide in a single formulation, but that preparation of such a formulation requires special care that has not heretofore been provided in the art.

DESCRIPTION OF THE INVENTION

In accordance with the present invention, a pharmaceutical formulation is provided which includes a combination of metformin and glipizide in a single formulation, wherein the glipizide content is uniform, and which formulation controls moisture so that the glipizide does not hydrolyze, yet the metformin is compressable.

In addition, in accordance with the present invention, a method is provided for treating diabetes, especially type 2 diabetes which includes the step of administering to a patient in need of treatment, a therapeutically effective pharmaceutical formulation of the invention which includes a combination of metformin and glipizide in dosages as described herein, in a single formulation wherein the glipizide content is uniform, and which formulation controls moisture so that the glipizide does not hydrolyze, yet the metformin is compressable.

In addition, in accordance with the present invention, a method is provided for decreasing fasting plasma glucose, decreasing insulin resistance, decreasing hemoglobin A1c, increasing post-prandial insulin and/or decreasing post-prandial glucose excursion in a human diabetic patient, which includes the step of administering to a human patient the pharmaceutical formulation of the invention which includes a combination of metformin/glipizide as described herein.

The pharmaceutical compositions of the present invention may take the form of several different embodiments. Thus, in one embodiment of the present invention, a pharmaceutical composition is provided wherein the metformin and glipizide are formulated together in a bilayered tablet which includes a first layer and a second layer. Glipizide, in the form of micronized particles will be present in the first layer together with optional excipients as described hereinafter, while the metformin will be present in the second layer which optionally may include one or more excipients as described hereinafter.

In addition, the bilayered tablet of the invention may include an outer protective coating or finishing layer as described hereinafter.

Another embodiment of the present invention comprises a cored tablet which includes a core and a buffering layer or outer coat which can be compressed onto the core as a dry coat. The core will preferably include glipizide particles while the buffering layer or outer coat will include metformin together with one or more optional excipients.

The so-described cored tablet may also optionally include an outer protective coating or finishing layer as described hereinafter.

In addition, in accordance with the present invention, a pharmaceutical composition is provided which is in the form of a tablet or capsule which includes a mixture of glipizide particles having an enteric coating and metformin.

In yet another embodiment of the pharmaceutical composition of the present invention, enteric coated glipizide particle as described above may be further coated with a protective coating or finishing layer. The double coated particles of glipizide can be mixed with metformin and the mixture can be encapsulated or tableted as described herein. The glipizide and the metformin do not need to be mixed together; these can even be encapsulated separately into the same capsule shells in two shots.

Another embodiment of the pharmaceutical composition of the invention includes particles of enteric coated glipizide and enteric coated metformin, in the same dosage form such as compressed tablets or capsules.

The tablets containing the enteric coated particles of glipizide and metformin may also include an outer protective coating or finishing layer.

In a further embodiment of the pharmaceutical composition of the invention, the composition of the invention may comprise a mixture of glipizide particles and metformin; the above mixture may take the form of compressed tablets (which may be film coated) or capsules (where the mixture can be encapsulated separately in two shots in the same capsule shells).

Preferred daily dosages of the combination of metformin and glipizide will be in the range from about 250 to about 2500 mg metformin, preferably in about 250 mg increments (e.g., 250, 500, 750, 1000, 1250, 2000 and 2500 mg), and from about 1.25 to about 25 mg glipizide, preferably in about 2.25 mg increments (e.g., 1.25, 2.5, 5.0, 7.25, 10.0, 12.5, 15.0, 20.0 and 250 mg). Especially preferred tablet strengths include 250/1.25 mg, 250/2.5 mg, 500/2.5 mg and 500/5 mg.

DETAILED DESCRIPTION OF THE INVENTION

The term "diabetes" as employed herein, refers to type 2 (or Type II) diabetes or non-insulin dependent diabetes mellitus (NIDDM).

The term "metformin" as employed herein refers to metformin or a pharmaceutically acceptable salt thereof such as the hydrochloride salt, the metformin (2:1) fumarate salt, and the metformin (2:1) succinate salt as disclosed in U.S. Pat. No. 6,031,004, the hydrobromide salt, the p-chlorophenoxy acetate or the embonate, and other known metformin salts of mono and dibasic carboxylic acids including those disclosed in U.S. Pat. No. 3,174,901, all of which salts are collectively referred to as metformin. It is preferred that the metformin employed herein be the metformin hydrochloride salt, namely, that marketed as Glucophage® (trademark of Bristol-Myers Squibb Company).

The term "post-prandial excursion" as employed herein refers to the difference between post-prandial glucose (PPG) and fasting plasma glucose (FPG).

It is believed that the use of metformin in combination with glipizide in accordance with the present invention produces antihyperglycemic results greater than that possible from each of these agents alone and greater than the combined additive anti-hyperglycemic effects produced by these agents.

Metformin will be employed in a weight ratio to the glipizide in the range from about 2000:1 to about 10:1, preferably from about 400:1 to about 100:1, more preferably from about 200:1 to about 100:1.

Glipizide may be employed in the formulation in amounts and dosing as indicated in the Physicians' Desk Reference.

In carrying out the present invention, pharmaceutical formulations or compositions will be employed containing metformin and glipizide in association with a pharmaceutical vehicle or diluent. The formulations can be formulated employing conventional solid or liquid vehicles or diluents and pharmaceutical additives of a type appropriate to the mode of administration. The formulations of the invention can be administered to mammalian species including humans, monkeys, dogs, etc., in the form of tablets or capsules. The dose can be administered in a single dose or in the form of individual doses from 1-4 times per day.

The above dosage forms may also include the necessary physiologically acceptable carrier material, excipient, lubricant, buffer, antibacterial, bulking agent (such as mannitol), anti-oxidants (ascorbic acid or sodium bisulfite) or the like.

The dose administered should be carefully adjusted according to the age, weight, and condition of the patient, as well as the dosage form and regimen, and the desired result.

The combination of the metformin or salt thereof and glipizide may be formulated separately or, where possible, in a single formulation employing conventional formulation procedures.

The various formulations of the invention may optionally include one or more fillers or excipients in an amount within the range of from about 0 to about 90% by weight and preferably from about 1 to about 80% by weight such as lactose, sugar, corn starch, modified corn starch, mannitol, sorbitol, inorganic salts such as calcium carbonate and/or cellulose derivatives such as wood cellulose and microcrystalline cellulose.

One or more binders may be present in addition to or in lieu of the fillers in an amount within the range of from about 0 to about 35% and preferably from about 0.5 to about 30% by weight of the composition. Examples of such binders which are suitable for use herein include polyvinylpyrrolidone (molecular weight ranging from about 2500 to about 3,000,000 and preferably about 50,000), lactose, starches such as corn starch, modified corn starch, sugars, gum acacia and the like as well as a wax binder in finely powdered form (less than 500 microns) such as carnauba wax, paraffin, spermaceti, polyethylenes or microcrystalline wax.

Tablets of the invention will include one or more tableting lubricants in an amount within the range of from about 0.2 to about 8% and preferably from about 0.5 to about 2% by weight of the composition, such as magnesium stearate, stearic acid, palmitic acid, calcium stearate, talc, carnauba wax and the like. Other conventional ingredients which may optionally be present include preservatives, stabilizers, anti-adherents or silica flow conditioners or glidants, such as Syloid brand silicon dioxide as well as FD&C colors.

Tablets of the invention may also include a coating layer which may comprise from 0 to about 15% by weight of the tablet composition. The coating layer may comprise any conventional coating formulations and will include one or more film-formers or binders, such as a hydrophilic polymer like methylcellulose, and/or a hydrophobic polymer like methacrylic acid esters neutral polymer, ethyl cellulose, cellulose acetate, polyvinyl alcohol-maleic anhydride copolymers, β-pinene polymers, glyceryl esters of wood resins and the like and one or more plasticizers, such as triethyl citrate, diethyl phthalate, propylene glycol, glycerin, butyl phthalate, castor oil and the like. Both core tablets as well as coating formulations may contain aluminum lakes, titanium dioxide and/or iron oxides to provide color.

The film formers may be applied from a solvent system containing one or more solvents including water, alcohols like methyl alcohol, ethyl alcohol or isopropyl alcohol, ketones like acetone, or ethylmethyl ketone, chlorinated hydrocarbons like methylene chloride, dichloroethane, and 1,1,1-trichloroethane.

Where a color is employed, the color may be applied together with the film former, plasticizer and solvent compositions.

The finished dosage form is either a compressed tablet or a hard gelatin capsule, preferably a tablet. The tablet may be optionally film coated. The total amount of drug per dosage unit would be such as to offer a dosage form of convenient size for patients. These tablets can, of course, be scored to provide for fractional doses in some cases.

In forming the pharmaceutical composition of the invention in the form of a bilayered tablet, the first layer containing glipizide will also preferably include bulking agents such as lactose, microcrystalline cellulose, wood cellulose, corn starch, modified corn starch, calcium phosphate, sugar, dextrose, mannitol or sorbitol. The bulking agent will be present in an amount from about 1 to about 90%, preferably from about 5 to about 85% by weight of the first layer containing glipizide.

The first layer may also include a tableting lubricant, such as zinc stearate, magnesium stearate, calcium stearate, talc, carnauba wax, stearic acid, palmitic acid or hydrogenated vegetable oils and fats, in an amount within the range from about 0.01 to about 4%, and preferably 0.02 to about 2% by weight of the first layer.

The second layer of the bilayered tablet containing metformin will usually include a bulking agent such as lactose, microcrystalline cellulose, modified corn starch, calcium phosphate or other bulking agent as set out above for the first layer, in an amount within the range from about 1 to about 90%, preferably from about 5 to about 85% by weight of the second layer. In addition, the second layer may include a binder such as corn starch, pregelatinized starch, polyvinyl pyrrolidone (PVP), hydroxypropylmethyl cellulose (HPMC), ethyl cellulose, cellulose acetate and the like, in an amount within the range from about 0.5 to about 20%, preferably from about 1 to about 10% by weight of the second layer, and a tableting lubricant such as magnesium stearate, zinc stearate, or other lubricant as set out above with respect to the first layer in an amount from about 0.01 to about 4%, preferably from about 0.02 to about 2% by weight of the second layer.

The buffering agents present in the second layer may include conventional acid buffers such as calcium carbonate, magnesium oxide, magnesium carbonate, magnesium hydroxide, aluminum hydroxide, dihydroxyaluminum sodium carbonate, aluminum magnesium hydroxide sulfate or aluminum hydroxide magnesium carbonate co-dried gel, or mixtures of one or more thereof, in amounts as needed. Thus, amounts of buffering agent within the range from about 10 to about 1000 mg, preferably from about 50 to about 500 mg will be employed depending upon the amount of glipizide present in the first layer.

In forming a bilayered tablet of the invention, the first layer containing glipizide may be prepared by conventional wet granulation or dry granulation (compaction) techniques.

The second layer containing metformin may be prepared by conventional wet granulation or dry granulation (compaction) techniques.

The first and second layers may then be compressed and combined to form a bilayered tablet employing conventional bilayer tableting equipment.

Other conventional ingredients which may optionally be present in either of the two layers include preservatives, stabilizers, anti-adherents or silica flow conditioners or glidants, such as Syloid brand silicon dioxide as well as antioxidants such as Vitamin E, Vitamin C, and folic acid, Vitamin $B_6$ and Vitamin $B_{12}$.

The bilayer tablet of the invention may also include an outer protective coating layer which may comprise from 0 to about 15% by weight of the bilayer tablet. The outer protective coating layer which is applied over the bilayered tablet may comprise any conventional coating formulations and will include one or more film-formers or binders, such as a hydrophilic polymer like hydroxy-propylmethyl cellulose (HPMC) and a hydrophobic polymer like ethyl cellulose, cellulose acetate, polyvinyl alcohol-maleic anhydride copolymers, acrylic copolymers, β-pinene polymers, glyceryl esters of wood resins and the like, and one or more plasticizers, such as polyethylene glycol, triethyl citrate, diethyl phthalate, propylene glycol, glycerin, butyl phthalate, castor oil and the like.

The film formers are applied from a solvent system containing one or more solvents including water, alcohols like methyl alcohol, ethyl alcohol or isopropyl alcohol, ketones like acetone, or ethylmethyl ketone, chlorinated hydrocarbons like methylene chloride, dichloroethane, and 1,1,1-trichloroethane.

The pharmaceutical composition of the invention in the form of a cored tablet wherein the glipizide forms the core, and metformin is present in a surrounding coat layer, may be prepared employing conventional cored tablet technology. Thus, the glipizide containing core (including excipients and other ingredients as described for the first layer in the bilayered tablet of the invention) may be formed in a manner similar to the first layer of the bilayered tablet as described hereinbefore. The layer containing metformin as well as excipients and other ingredients (as described hereinbefore for the second layer of the bilayered tablet of the invention) may be compressed onto the core as a dry coat.

The so-formed cored tablet may be coated with an outer protective coating layer as described above for the bilayered tablet.

Another embodiment of the pharmaceutical composition of the invention is formed of tablets or capsules containing a mixture of enteric coated glipizide particles and metformin.

The glipizide particles can be coated with conventional enteric polymer coatings in aqueous or non-aqueous systems. For example, Eudragit L-30D-55 (acrylic acid copolymers-Rohm Pharma) (5 to 25% solids) containing 10 to 15% of diethylphthlate (w/w) as plasticizer can be used in an aqueous system.

Other conventional enteric polymer coating systems may be employed such as Eudragit R and S series resins, (acrylic acid copolymers-Rohm Pharma), cellulose acetate phthalate, cellulose acetate maleate, cellulose acetate succinate, hydroxypropylmethyl cellulose phthalate, hydroxypropylmethylcellulose acetate succinate, and the like, and a suitable plasticizer such as triethyl citrate, diethyl phthalate, tributyl citrate, triacetin, dibutyl phthalate dibutyl sebicate, Myvacet 940, and other commonly used plasticizers as may be suitable for the particular enteric polymers can be used. It will be appreciated that any polymer with suitable plasticizer can be used in an aqueous or non-aqueous system to form an enteric coating on the glipizide particle.

In another embodiment of the pharmaceutical composition of the invention, the enteric coated glipizide particles described above may be further coated with an outer protective finishing coat or layer as described hereinbefore.

The double coated glipizide particles can be mixed with metformin and the mixture can be encapsulated or tableted as described above.

In yet another embodiment of the pharmaceutical composition of the invention, glipizide is enteric coated as described above and the metformin can optionally be enteric coated. The metformin can be coated in the form of pure drugs or after spheronization or agglomeration. The particles for coating do not need to be perfectly spherical. These could be rods or irregular particles. The enteric coated particles of the two agents (glipizide and metformin) can be tableted or encapsulated together. As described above, appropriate excipients (fillers, binders, disintegrants, and lubricant, etc.) can be used to facilitate tableting.

In yet another embodiment, glipizide particles can be mixed with enteric coated particles of metformin, and the mixture can be tableted or encapsulated, or the two granules can be encapsulated in two shots in the same capsule shells.

In still a further embodiment, neither the glipizide particles nor the metformin particles need to be enteric coated.

Examples of typical ingredients are shown in Table 1.

Examples of typical ingredients used in manufacturing metformin/glipizide combination tablets is shown below in Table 1. Included in the table are alternative ingredients as well as commonly used ranges.

| Ingredient | Function | Alternatives | Commonly used amounts (% w/w) |
|---|---|---|---|
| Metformin | Active ingredient | | 50% to 95% |
| Glipizide | Active ingredient | | 0.1% to 2.5% |
| Microcrystalline cellulose | Diluent | Lactose, calcium phosphate, mannitol | 1% to 60% |
| Povidone | Binder | Hydroxypropyl cellulose, methylcellulose, hydroxypropyl-methylcellulose, starch, gelatin, guar gum, zanthum gum, pregelatinized starch | 0.5% to 10% |
| Croscarmellose sodium | Disintegrant | Crospovidone, sodium starch glycolate, pregelatinized starch, starch | 0.5% to 10% |
| Magnesium stearate | Lubricant | Stearic acid, calcium stearate, zinc stearate, sodium stearyl fumarate | 0.1% to 5% |
| HPMC | Coating | Ethyl cellulose, methacrylic copolymers, hydroxypropyl cellulose | 0.5% to 10% |
| Water | Granulating and coating solvent | Ethanol, methanol | Used for the process; removed by drying |

The preferred pharmaceutical formulations of the invention in the form of a tablet may be obtained generally by a process which includes the steps of a) forming granules by wet granulation of a mixture of metformin and glipizide with some of the excipients (e.g., microcrystalline cellulose, povidone and croscarmellose sodium), b) blending the granules with additional microcrystalline cellulose and magnesium stearate and diluent, and c) tableting the blend thus obtained into tablets.

The mixture used for forming the granules may include a granulating binder. The granulating binder is preferably a polyvinylpyrrolidone such as, for example, a polyvinylpyrrolidone having a molecular weight of 50,000. The polyvinylpyrrolidone may be used in a proportion of 2 to 4% by weight with respect to the final tablet.

After the granulating step, the granules may be sieved and dried.

The granules may then be blended with a diluent and tableting aid. The diluent may be a conventional filler usually used for making tablets, such as microcrystalline cellulose. The tableting aid may be a conventional material, such as magnesium stearate.

The tablets thus obtained may then optionally be coated with a hydrophilic cellulose polymer and talc. The hydrophilic cellulose polymer is preferably 2-hydroxypropyl methylcellulose.

Typical formulations for metformin/glipizide film coated tablets of different strengths appear below in table 2.

TABLE 2

| | Metformin/glipizide | | | | | |
|---|---|---|---|---|---|---|
| | 500/2.5 mg | | 500/5 mg | | 250/2.5 mg | |
| Ingredients | mg/tab | %, w/w | mg/tab | %, w/w | mg/tab | %, w/w |
| Tablet Core | | | | | | |
| Metformin Hydrochloride with 0.5% Mg Stearate Premix | 502.5 | 83.75 | 502.5 | 83.75 | 251.25 | 83.75 |
| Glipizide | 2.5 | 0.417 | 5.0 | 0.834 | 2.5 | 0.834 |
| Croscarmellose Sodium NF | 14 | 2.33 | 14 | 2.33 | 7 | 2.33 |
| Povidone | 20 | 3.33 | 20 | 3.33 | 10 | 3.33 |
| Purified Water[4] | q.s. | | q.s. | | q.s. | |
| Microcrystalline Cellulose NF | 56.5 | 9.42 | 54.0 | 9.00 | 27 | 9.00 |

TABLE 2-continued

| Ingredients | mg/tab | %, w/w | mg/tab | %, w/w | mg/tab | %, w/w |
|---|---|---|---|---|---|---|
| Magnesium Stearate NF | 4.5 | 0.75 | 4.5 | 0.75 | 2.25 | 0.75 |
| TOTAL TABLET CORE | 600 | 100 | 600 | 100 | 300 | 100 |
| Film Coating[B] | | | | | | |
| Opadry White | 21 | 3.5 | | | | |
| Opadry Pink 32K14883 (lighter) | | | 21 | 3.5 | 10.5 | 3.5 |
| Opadry Pink YS-1-14778-A (darker) | | | | | | |
| Purified Water[A] | 119 | | 119 | | 59.5 | |
| Total Tablet Weight | 621 | | 621 | | 310.5 | |

| | Metformin/glipizide | | | | | |
|---|---|---|---|---|---|---|
| | 500/7.5 mg | | 250/1.25 mg | | 500/1.25 mg | |
| Ingredients | mg/tab | %, w/w | mg/tab | %, w/w | mg/tab | %, w/w |
| Tablet Core | | | | | | |
| Metformin Hydrochloride with 0.5% Mg Stearate Premix | 502.5 | 83.75 | 251.25 | 83.75 | 502.5 | 83.75 |
| Glipizide | 7.5 | 1.250 | 1.25 | 0.417 | 1.25 | 0.208 |
| Croscarmellose Sodium NF | 14 | 2.33 | 7 | 2.33 | 14 | 2.33 |
| Povidone | 20 | 3.33 | 10 | 3.33 | 20 | 3.33 |
| Purified Water[A] | q.s. | | q.s. | | q.s. | |
| Microcrystalline Cellulose NF | 51.5 | 8.58 | 28.25 | 9.42 | 57.75 | 9.63 |
| Magnesium Stearate NF | 4.5 | 0.75 | 2.25 | 0.75 | 4.5 | 0.75 |
| TOTAL TABLET CORE | 600 | 100 | 300 | 100 | 600 | 100 |
| Film Coating[B] | | | | | | |
| Opadry White | | | 10.5 | 3.5 | 21 | 3.5 |
| Opadry Pink 32K14883 (lighter) | | | | | | |
| Opadry Pink YS-1-14778-A (darker) | 21 | 3.5 | | | | |
| Purified Water[A] | 119 | | | | | |
| Total Tablet Weight | 621 | | 310.5 | | 621.0 | |

Note:
[A]Water was removed during processing.
[B]The actual amount of coating may vary based on a range of 3.0-4.0% of the film coat.

In whatever embodiment, the formulation is typically administered so as to provide from about 250 to about 500 mg metformin one to four times daily. The glipizide will preferably be administered in an amount from about 1.25 to about 5.0 mg one to four times daily, with a maximum of up to about 20.0 mg daily.

The pharmaceutical formulation of the invention is an adjunct to diet and exercise to improve glycemic control in patients with type 2 diabetes mellitus.

The ADA recommends a treatment goal of $HbA_{1c}<7\%$ (ADA. *Diabetes Care* 21 [Suppl. 1]: S23-S31, 1998) in order to reduce the risk of complications of type 2 diabetes mellitus, including coronary heart disease and microvascular complications.

Dosage of the formulation of the invention must be individualized on the basis of both effectiveness and tolerance. It is preferably given with meals and should be started at a low dose, with gradual dose escalation. Ideally, the response to therapy should be evaluated using $HbA_{1c}$ (glycosylated hemoglobin) which is a better indicator of long-term glycemic control than FPG (fasting plasma glucose) alone. The therapeutic goal in all patients with type 2 diabetes mellitus should be to improve glycemic control, including FPG, postprandial glucose and $HbA_{1c}$ levels, to normal or as near normal as possible. Patients should be titrated to achieve the ADA goal of $HbA_{1c}<7\%$ following the dosing recommendations up to the maximum recommended dose. (ADA. *Diabetes Care* 21 [Suppl. 1]: S23-S32, 1998).

For patients with type 2 diabetes whose hyperglycemia cannot be satisfactorily managed with diet and exercise alone, the recommended starting dose is 2.5 mg/250 mg once a day with a meal. As initial therapy in patients with baseline FPG>280 mg/dL, a starting dose of 2.5 mg/500 mg once daily should be considered. Dosage increases to achieve adequate glycemic control should be made in increments of one tablet per day every two weeks up to a maximum of approximately 10 mg/1000 mg or 10 mg/2000 mg per day given in divided doses.

For patients not adequately controlled on either glipizide (or another sulfonylurea) or metformin alone, the recommended starting dose is 2.5 mg/500 mg or 5 mg/500 mg twice daily with the morning and evening meals. In order to avoid hypoglycemia, the starting dose should not exceed the daily doses of glipizide or metformin already being taken. The daily dose should be titrated in increments of no more than 5 mg/500 mg up to the minimum effective dose to achieve adequate control of blood glucose or to a maximum dose of about 20 mg/2000 mg per day.

For patients previously treated with combination therapy of glipizide (or another sulfonylurea) plus metformin, the starting dose should not exceed the daily dose of glipizide (or equivalent dose of another sulfonylurea) and metformin already being taken. The decision to switch to the nearest equivalent dose or to titrate should be based on clinical judgment. Patients should be monitored closely for signs and symptoms of hypoglycemia following such a switch and the dose should be titrated to achieve adequate control of blood glucose.

EXAMPLE

Tablets containing metformin/glipizide combinations were prepared as described below for 250 mg/2.5 mg:

| Batch formula, Metformin HCl/glipizide tablet, 250/2.5 mg | | |
|---|---|---|
| Materials | mg/tab. | Gram/5 kg batch |
| Intragranular | | |
| Metformin HCl w 0.5% MgS | 251.25 | 4187.5 |
| Glipizide | 2.5 | 41.666 |
| Croscarmellose sodium | 7.0 | 116.7 |
| Povidone (PVP) | 10.00 | 166.7 |
| Water[A] | q.s. | q.s. |
| Extragranular | | |
| Microcrystalline cellulose (PH-102 grade) | 27.0 | 450.0 |
| Magnesium Stearate | 2.25 | 37.5 |
| Core Tablet Weight | 300.0 | 5000.0 |
| Film Coating | | |
| Opadry Pink 32K14883 | 10.5 | 175.0 |
| Water | q.s. | q.s. |
| Total Tablet Weight | 310.5 | 5175.0 |

[A]Water is used for granulation and removed by drying from the tablets.
B. Removed during coating.

Croscarmellose sodium and glipizide were dispersed together followed by blending with about 790 g metformin hydrochloride/magnesium stearate (99.5%:0.5% w/w) in a mixer at low speed for 10 minutes. About ½ of the dry mix, ½ of the remaining metformin, the other ½ of the dry mix and the final ½ of the metformin were layered in the mixer and mixed for an additional 10 minutes. The resultant dry mix was granulated in a high shear mixer with an aqueous povidone solution and granules were dried in a fluid bed dryer at approximately 40° C. with the residual moisture between about 2.0% and 3.0% w/w. The dried granulation was reduced with a #18 mesh screen oscillator or a comil and mixed with the microcrystalline cellulose in a V-blender. Magnesium stearate was added into the V-blender and blended for 5 minutes.

The resultant blend was compressed into tablets on a suitable tablet press.

The tablets were then preheated in a perforated coating pan at 40° C. to 60° C. for 15 minutes. Then the coating pan was rotated at 4 to 8 rpm and the spraying of the film coating begun. When the coating was approximately 3.5%, the spray was stopped. The pan was allowed to rotate until the tablets cooled down.

If the granules were oven-dried during the drying process, they were re-wetted by spraying a calculated amount of water in a mixer. The moisture in the granules should be 2% to 3% w/w to make tablets with acceptable hardness and to prevent caping.

During the coating process, tablets are preheated to drive the excess moisture out and to harden the tablets so that tablets will not crumble when rotated in the coating pan. The reduction of the moisture is also used to minimize hydrolysis of glipizide. Once the coating is applied and dried, the coating layer will act as a barrier against moisture and will minimize the hydrolysis of glipizide.

What is claimed is:

1. A method for treating type 2 diabetes which comprises administering to a patient in need of treatment a therapeutically effective amount of a pharmaceutical composition comprising a single dosage formulation of metformin and glipizide said formulation containing from 2 to 3% by weight moisture, said formulation being in the form of a tablet designed to control moisture so that the glipizide does not hydrolyze and said metformin is compressible, said tablet further including an outer protective coating or finishing layer surrounding said tablet, said composition being devoid of an enteric coating.

2. The method as defined in claim 1 wherein the amount of metformin and glipizide in the combination is that employed in generally accepted medical practice for treating diabetes.

3. The method as defined in claim 2 wherein the dosage of metformin administered is from about 250 mg to about 2500 mg/day.

4. The method as defined in claim 3 wherein the metformin is administered in 250 mg increments.

5. The method as defined in claim 2 wherein the dosage of glipizide administered is from about 1.25 to about 25 mg/day.

6. The method as defined in claim 5 wherein the glipizide is administered in about 2.25 mg increments.

7. The method as defined in claim 1 wherein the metformin is employed in a weight ratio to glipizide within the range from about 1000:1 to about 100:1.

8. The method as defined in claim 1 wherein the pharmaceutical composition comprises a dosage of metformin of from about 250 to about 2500 mg/day and a dosage of glipizide from about 1.25 to about 25 mg/day.

9. The method as defined in claim 1 wherein the metformin is employed in a weight ratio to the glipizide within the range from about 400:1 to about 100:1.

10. The method as defined in claim 1 wherein the dosage of metformin is 250 mg and the dosage of glipizide is 1.25 mg.

11. The method as defined in claim 1 wherein the dosage of metformin is 250 mg and the dosage of glipizide is 2.50 mg.

12. The method as defined in claim 1 wherein the dosage of metformin is 500 mg and the dosage of glipizide is 2.50 mg.

13. The method as defined in claim 1 wherein the dosage of metformin is 500 mg and the dosage of glipizide is 5.00 mg.

* * * * *